US006656978B2

(12) United States Patent
Shiroto et al.

(10) Patent No.: US 6,656,978 B2
(45) Date of Patent: Dec. 2, 2003

(54) PROCESS OF PRODUCING LIQUID HYDROCARBON OIL OR DIMETHYL ETHER FROM LOWER HYDROCARBON GAS CONTAINING CARBON DIOXIDE

(75) Inventors: Yoshimi Shiroto, Yokohama (JP); Kenichi Kawazuishi, Yokohama (JP); Masato Tauchi, Fujisawa (JP); Mitsunori Shimura, Yokohama (JP)

(73) Assignee: Chiyoda Corporation (JP)

( * ) Notice: Subject to any disclaimer, the term of this patent is extended or adjusted under 35 U.S.C. 154(b) by 58 days.

(21) Appl. No.: 09/825,967

(22) Filed: Apr. 5, 2001

(65) Prior Publication Data

US 2003/0036572 A1 Feb. 20, 2003

(51) Int. Cl.⁷ .............................. C07C 27/00; C07C 1/02
(52) U.S. Cl. ....................... 518/715; 518/702; 518/704; 252/373
(58) Field of Search .................... 252/373; 518/702, 518/704, 715

(56) References Cited

U.S. PATENT DOCUMENTS

| | | | |
|---|---|---|---|
| 3,222,132 A | 12/1965 | Dowden | 423/652 |
| 4,367,166 A | 1/1983 | Fujitani et al. | 423/652 |
| 4,415,484 A | 11/1983 | Setzer et al. | 423/651 |
| 5,246,791 A | 9/1993 | Fisher et al. | 429/16 |
| 5,395,406 A | 3/1995 | Clavenna et al. | 48/198.7 |
| 5,604,396 A | 2/1997 | Watanabe et al. | 313/485 |
| 5,614,163 A | 3/1997 | Bhattacharyya et al. | 423/418.2 |
| 5,919,425 A | 7/1999 | Nguyen et al. | 423/210 |
| 5,958,297 A | 9/1999 | Primdahl | 252/373 |
| 5,989,457 A | 11/1999 | Seshan et al. | 252/373 |
| 6,277,894 B1 * | 8/2001 | Agee et al. | 518/700 |

FOREIGN PATENT DOCUMENTS

| | | | |
|---|---|---|---|
| EP | 0974551 A1 | * | 1/2000 |
| GB | 2182932 | | 5/1987 |
| JP | 58-49602 | | 3/1983 |
| JP | 60-202740 | | 10/1985 |
| JP | 2-227141 | | 9/1990 |
| JP | 2-307802 | | 12/1990 |
| JP | 4-331704 | | 11/1992 |
| JP | 9-131533 | | 5/1997 |
| WO | 9424042 | | 10/1994 |
| WO | 9616737 | | 6/1996 |

OTHER PUBLICATIONS

Rostrup–Nielsen et al, CO2–Reforming oF Methane over Transition Metals, Journal of Catalysis 144, 38–49 (1993).

* cited by examiner

*Primary Examiner*—J. Parsa
(74) *Attorney, Agent, or Firm*—Lorusso, Loud & Kelly

(57) ABSTRACT

A process for the production of a liquid hydrocarbon oil from a gas feed containing a lower hydrocarbon and $CO_2$, wherein the gas feed is mixed with $H_2O$ to obtain a mixed gas having specific $CO_2$, $H_2O$ and lower hydrocarbon contents. The mixed gas is contacted with a Rh, Ru/MgO catalyst having a specific surface area of 5 $m^2/g$ or less to produce a synthesis gas with a carbon conversion efficiency Cf of at least 50%. The thus obtained synthesis gas having a $H_2/CO$ molar ratio of 1.5–2.5 is reacted in the presence of a Fischer-Tropsch catalyst to obtain a liquid hydrocarbon oil, while the synthesis gas having a $H_2/CO$ molar ratio of 0.5–1.5 is reacted in the presence of one or more catalysts having methanol synthesizing, dehydrating and CO shift reaction activities to obtain dimethyl ether.

8 Claims, No Drawings

PROCESS OF PRODUCING LIQUID HYDROCARBON OIL OR DIMETHYL ETHER FROM LOWER HYDROCARBON GAS CONTAINING CARBON DIOXIDE

BACKGROUND OF THE INVENTION

This invention relates to a process for the production of a liquid hydrocarbon oil or dimethyl ether from a lower hydrocarbon gas containing carbon dioxide.

It is well known to convert a lower hydrocarbon gas (HC gas) to a synthesis gas containing CO (carbon monoxide) and $H_2$ (hydrogen) by reforming reaction thereof with $H_2O$ (steam or water) in the presence of $CO_2$ (carbon dioxide). It is also known to produce a liquid hydrocarbon oil (HC oil) having 5 or more carbon atoms suitable for use as a fuel oil by Fischer-Tropsch synthesis (FT synthesis) from the synthesis gas and to produce dimethyl ether from the synthesis gas.

U.S. Pat. No. 4,640,766 discloses reforming in the presence of a Ni catalyst. This process has a problem of carbon deposition on the catalyst, which causes catalytic poisoning.

U.S. Pat. No. 5,621,155 and U.S. Pat. No. 5,620,670 use a Fe catalyst having a high CO shift reaction activity in FT synthesis. About a half of CO in the synthesis gas is lost in the form of $CO_2$ and, hence, the carbon conversion efficiency is at most 50%. The disclosed process uses a Ni catalyst in reforming of HC gas with $CO_2$ and, thus, has a problem of carbon deposition on the catalyst.

Industrial actually employed reforming processes are performed at 600–1,000° C. with a steam ratio $[H_2O]/[C]$ (ratio of steam to carbon of raw material HC feed) of 2–5. While a lower steam ratio is desired from the standpoint of energy saving, carbon deposition on the catalyst significantly occurs as the steam ratio becomes lower than 2. A higher steam ratio is needed as $CO_2$ concentration in the feed gas increases. This problem is encountered in the above-described conventional processes.

EP-A-0974551 discloses a process for producing a synthesis gas by reacting a hydrocarbon with $H_2O$ and/or $CO_2$ using a catalyst having a specific surface area of 25 $m^2/g$ or less and comprising a magnesium oxide-containing carrier and Rh and/or Ru supported on the carrier in an amount of 0.0005–0.1 mole %, in terms of elemental metal, based on the carrier. This process is promising because of freedom from the problem of carbon deposition on the catalyst.

SUMMARY OF THE INVENTION

In accordance with one aspect of the present invention, there is provided a process for the production of a liquid hydrocarbon oil from a lower hydrocarbon gas and carbon dioxide, comprising the steps of:

(a) mixing a gas feed, containing a lower hydrocarbon having 1–4 carbon atoms and 10–50 mole % of $CO_2$ based on a total mole of the $CO_2$ and the lower hydrocarbon, with $H_2O$ to obtain a mixed gas having contents of the $CO_2$, $H_2O$ and lower hydrocarbon satisfying the following condition:

$$0.5 \leq ([CO_2]+[H_2O])/[C] \leq 2.5$$

wherein $[CO_2]$ represents the moles of the $CO_2$, $[H_2O]$ represents the moles of the $H_2O$ and $[C]$ represents the moles of carbon of the lower hydrocarbon;

(b) contacting said mixed gas with a catalyst at a temperature of 600–1,000° C. and a pressure of 10–75 atm to produce a synthesis gas with a carbon conversion efficiency Cf of at least 50% and a synthesis gas production efficiency Yf of at least 80%, said synthesis gas production efficiency Yf being represented by the following formula:

$$Yf=\{([CO]+[H_2])/([C]+[CO_2]+[H_2])\} \times 100\%$$

wherein [CO] represents the moles of CO in said synthesis gas, $[H_2]$ represents the moles of $H_2$ in said synthesis gas, and $[CO_2]$, $[H_2O]$ and $[C]$ are as defined previously, said carbon conversion efficiency Cf being represented by the following formula:

$$Cf=\{[CO]/([C]+[CO_2])\} \times 100\%$$

wherein [CO], $[CO_2]$ and [C] are as defined previously, said synthesis gas having a molar ratio of hydrogen to carbon monoxide of 1.5–2.5, said catalyst having a specific surface area of 5 $m^2/g$ or less and comprising a magnesium oxide-containing carrier and at least one catalytic metal selected from the group consisting of rhodium and ruthenium and supported on said carrier in an amount of 10–5,000 ppm, in terms of elemental metal, based on the weight of said carrier;

(c) reacting said synthesis gas in the presence of a Fischer-Tropsch catalyst having a low CO shift reaction activity to obtain a product containing a liquid hydrocarbon oil; and (d) separating said liquid hydrocarbon oil from said product.

In another aspect, the present invention provides a process for the production of dimethyl ether from a lower hydrocarbon gas and carbon dioxide, comprising the steps of:

(a) mixing a gas feed, containing a lower hydrocarbon having 1–4 carbon atoms and 30–70 mole % of $CO_2$ based on a total mole of the $CO_2$ and the lower hydrocarbon, with $H_2O$ to obtain a mixed gas having contents of the $CO_2$, $H_2O$ and lower hydrocarbon satisfying the following condition:

$$0.5 \leq ([CO_2]+[H_2O])/[C] \leq 2.5$$

wherein $[CO_2]$ represents the moles of the $CO_2$, $[H_2O]$ represents the moles of the $H_2O$ and [C] represents the moles of carbon of the lower hydrocarbon;

(b) contacting said mixed gas with a catalyst at a temperature of 600–1,000° C. and a pressure of 10–75 atm to produce a synthesis gas with a synthesis gas production efficiency Yf of at least 80% and a carbon conversion efficiency Cf of at least 50%, said synthesis gas production efficiency Yf being represented by the following formula:

$$Yf=\{([CO]+[H_2])/([C]+[CO_2]+[H_2O])\} \times 100\%$$

wherein [CO] represents the moles of CO in said synthesis gas, $[H_2]$ represents the moles of $H_2$ in said synthesis gas, and $[CO_2]$, $[H_2O]$ and [C] are as defined previously, said carbon conversion efficiency Cf being represented by the following formula:

$$Cf=\{[CO]/([C]+[CO_2])\} \times 100\%$$

wherein [CO], $[CO_2]$ and [C] are as defined previously, said synthesis gas having a molar ratio of hydrogen to carbon monoxide of 0.5–1.5, said catalyst having a specific surface area of 5 m²/g or less and comprising a magnesium oxide-containing carrier and at least one catalytic metal selected from the group consisting of rhodium and ruthenium and supported on said carrier in an amount of 10–5,000 ppm, in terms of elemental metal, based on the weight of said carrier;

(c) reacting said synthesis gas in the presence of one or more catalysts having activities of methanol synthesis, methanol dehydration and CO shift reaction to obtain a product containing dimethyl ether; and (d) separating said dimethyl ether from said product.

It is an object of the present invention to provide a process which can produce HC oil on an industrial scale from HC gas by synthesis gas production and succeeding FT synthesis using a minimized size of the synthesis gas production reactor while utilizing not only HC gas but also $CO_2$ as a carbon source of the HC oil.

It is also an object of the present invention to provide a process which can produce dimethyl ether on an industrial scale from HC gas by synthesis gas production and succeeding dimethyl ether synthesis using a minimized size of the synthesis gas production reactor while utilizing not only HC gas but also $CO_2$ as a carbon source of the HC oil.

Other objects, features and advantages of the present invention will become apparent from the detailed description of the preferred embodiments of the invention to follow.

DETAILED DESCRIPTION OF THE PREFERRED EMBODIMENTS OF THE INVENTION

A raw material gas for the production of HC oil by FT synthesis should have a $H_2/CO$ ratio in the range of 1.5–2.5, ideally 2. Thus, it is important that the synthesis gas produced by reforming HC gas have a $H_2/CO$ ratio in the range of 1.5–2.5 in order to use the synthesis gas as such as a raw material.

One known process for obtaining a synthesis gas from HC gas such as methane is a partial oxidation process:

$$CH_4 + 1/2 O_2 \rightarrow 2H_2 + CO \quad (1)$$

When the HC gas feed contains $CO_2$, however, this process is ill-suited because of the necessity of removing $CO_2$ from the synthesis gas before introduction into a FT synthesis step.

Another known process for obtaining a synthesis gas from HC gas such as methane is a steam reforming process:

$$CH_4 + H_2O \rightarrow 3H_2 + CO \quad (2)$$

Since the synthesis gas has a $H_2/CO$ ratio 3, it is necessary to remove excess hydrogen from the synthesis gas before introduction into a FT synthesis step.

Autothermal reforming in which partial oxidation and steam reforming are combined is also known. With this process, it is necessary to remove $CO_2$ from the synthesis gas before introduction into a FT synthesis step.

A further known process for obtaining a synthesis gas from HC gas such as methane is a $CO_2$ reforming process:

$$CH_4 + CO_2 \rightarrow 2H_2 + 2CO \quad (3)$$

This process which gives a synthesis gas having a $H_2/CO$ ratio 1 is not suited as a raw feed for FT synthesis.

In the process of the present invention, the above steam reforming (2) and $CO_2$ reforming (3) are combined to yield a synthesis gas having a $H_2/CO$ ratio 1.5 to 2.5 which is suitable for FT synthesis.

A raw material gas for the production of dimethyl ether should have a $H_2/CO$ ratio in the range of 0.5–1.5, ideally 1. Thus, it is important that the synthesis gas produced by reforming HC gas have a $H_2/CO$ ratio in the range of 0.5–1.5 in order to use the synthesis gas as such as a raw material. For this purpose, the $CO_2$ reforming process utilizing the reaction (3) which gives a synthesis gas having a $H_2/CO$ ratio 1 is theoretically suited. In actual, however, reverse shift reaction:

$$H_2 + CO_2 \rightarrow H_2O + CO \quad (4)$$

occurs, so that the $H_2/CO$ ratio is lower than 1.

In the process of the present invention, the above steam reforming (2) and $CO_2$ reforming (3) are combined to yield a synthesis gas having a $H_2/CO$ ratio 0.5 to 1.5 which is suitable for the production of dimethyl ether.

In the production of HC oil and dimethyl ether, it is necessary that a synthesis gas production efficiency Yf represented by the formula shown below should be at least 80% in order that the synthesis gas production step which requires large energy consumption and high equipment costs should be performed with a reactor having a minimized size:

$$Yf = \{([CO]+[H_2])/([C]+[CO_2]+[H_2O])\} \times 100\%$$

wherein

[CO]: moles of the CO in the synthesis gas,

[$H_2$]: moles of the $H_2$ in the synthesis gas,

[$CO_2$]: moles of the $CO_2$ contained in the gas feed

[$H_2O$]: moles of the $H_2O$ in the mixed gas, and

[C]: moles of carbons of the gas feed.

It is also important that a carbon conversion efficiency Cf represented by the formula shown below should be at least 50% in order that the synthesis gas production step and the succeeding FT synthesis should be performed so that not only carbon from HC gas but also $CO_2$ is utilized as a carbon source for HC oil:

$$Cf = \{[CO]/([C]+[CO_2])\} \times 100\%$$

wherein

[CO], [$CO_2$] and [C] are as defined above.

In producing a synthesis gas for use as a raw material for the production of HC oil, it is important that the ([$CO_2$]+[$H_2O$])/[C] value should be in the range of 0.5–2.5 in order to attain Yf of 80% or more. The ([$CO_2$]+[$H_2O$])/[C] value is preferably 1–2. It is also important that the concentration of $CO_2$ in the HC gas feed should be 10–50 mole % based on the total moles of the $CO_2$ and the HC gas. When the $CO_2$ concentration is outside the above range, Cf of at least 50% cannot be attained. The $CO_2$ concentration of 20–40 mole % is preferred for reasons of increased Cf value. When methane is used as the raw material HC gas, the molar ratio of [$H_2O$]/[C] is preferably in the range of 0.4–1.5.

In producing a synthesis gas for use as a raw material for the production of dimethyl ether, it is important that the ([$CO_2$]+[$H_2O$])/[C] value should be in the range of 0.5–2.5 in order to attain Yf of 80% or more. The ([$CO_2$]+[$H_2O$])/[C] value is preferably 1–2. It is also important that the concentration of $CO_2$ in the HC gas feed should be 30–70 mole % based on the total moles of the $CO_2$ and the HC gas. When the $CO_2$ concentration is outside the above range, Cf of at least 50% cannot be attained. The $CO_2$ concentration of 40–60% is preferred for reasons of increased Cf value. When methane is used as the raw material HC gas, the molar ratio of [$H_2O$]/[C] is preferably in the range of 0.4–1.5.

The production of a synthesis gas may be performed by reacting HC gas containing $CO_2$ with $H_2O$ in the presence of a catalyst. As HC gas, a lower hydrocarbon having 1–4 carbon atoms such as methane, ethane, propane, butane or isobutane may be used. The use of a mixed hydrocarbon gas containing a major amount of methane and a minor amount of ethane, propane, butane, isobutane and other lower hydrocarbons is preferred. In the present invention, a natural gas containing $CO_2$ is advantageously used.

When the raw material HC gas contains an excess amount of $CO_2$, it is desirable to control the $CO_2$ content using a distillation tower operated at a pressure of 10–80 atm, preferably 20–50 atm. In the distillation tower, a $CO_2$-rich fraction is separated from a bottom, while a HC gas containing a controlled amount of $CO_2$ is discharged overhead therefrom. A pressure lower than 10 atm is disadvantageous because of formation of $CO_2$ solids in the tower. Too high a pressure in excess of 80 atm is disadvantageous because apparatus costs increase. The distillation is preferably performed at a tower top temperature of higher than −60° C. The high pressure $CO_2$-rich fraction discharged from the tower bottom may be recycled to a well.

The reaction of the HC gas for the formation of a synthesis gas is carried out at a temperature is 600–1,000° C., preferably 650–950° C. and a pressure of 10–70 atm, preferably 15–40 atm. When the reaction is performed with a fixed bed system, the gas space velocity (GHSV) is 1,000–10,000 $hr^{-1}$, preferably 2,000–8,000 $hr^{-1}$. The reaction may be carried out using any desired catalyst system such as a fixed bed system, a fluidized bed system, a suspended bed system or a moving bed system.

The catalyst used for the production of a synthesis gas has a specific surface area of 5 $m^2/g$ or less and comprises a magnesium oxide-containing carrier, and at least one catalytic metal selected rhodium and ruthenium and supported on the carrier in an amount of 10–5,000 ppm, in terms of elemental metal, based on the weight of the carrier. The MgO-containing carrier preferably consists essentially of magnesium oxide.

The catalyst having a specific surface area of 5 $m^2/g$ or less may be obtained by calcining a MgO-containing carrier before the support of a catalytic metal at 300–1,300° C., preferably 650–1,200° C. The specific surface area of the catalyst or the carrier metal oxide can be controlled by the calcination temperature and calcination time. The lower limit of the specific surface area is about 0.01 $m^2/g$.

Since the catalyst has a high degree of crystallinity and a small specific surface area and contains a very small amount of Rh and/or Ru, carbon deposition on the catalyst is considerably suppressed, while retaining high activity of reforming HC gas with $CO_2$ and $H_2O$.

In the catalyst of the present invention, the specific surface area of the catalyst is substantially the same as that of the carrier metal oxide. Thus, in the present specification, the term "specific surface area of a catalyst" is used as having the same meaning as "specific surface area of a carrier metal oxide thereof".

The term "specific surface area" referred to in the present specification in connection with a catalyst or a carrier metal oxide is as measured by the "BET method" at a temperature of 15° C. using a measuring device "SA-100" manufactured by Shibata Science Inc.

The catalyst of the present invention may be prepared by conventional methods. One preferred method of preparing the catalyst of the present invention is an impregnation method. To prepare the catalyst of the present invention by the impregnation method, a catalyst metal salt or an aqueous solution thereof is added to and mixed with an aqueous dispersion containing a carrier metal oxide. The carrier metal oxide is then separated from the aqueous solution, followed by drying and calcination. A method (incipient-wetness method) is also effective in which a carrier metal oxide is added with a solution of a metal salt little by little in an amount corresponding to a pore volume to uniformly wet the surface of the carrier, followed by drying and calcination. In these methods, a water soluble salt is used as the catalyst metal salt. Such a water soluble salt may be a salt of an inorganic acid, such as a nitrate or a hydrochloride, or a salt of an organic acid, such as an acetate or an oxalate. Alternately, a metal acetylacetonate, etc. may be dissolved in an organic solvent such as acetone and the solution may be impregnated into the carrier metal oxide. The drying is performed at a temperature of from room temperature to 200° C., preferably from room temperature to 150° C.

In the preparation of the catalyst of the present invention, the metal oxide used as a carrier may be a product obtained by calcining a commercially available metal oxide or a commercially available metal hydroxide. The purity of the metal oxide is at least 97% by weight, preferably at least 98% by weight. It is, however, undesirable that components which enhance carbon deposition activity or components which are decomposed under reducing conditions, such as metals, e.g. iron and nickel, and silicon dioxide ($SiO_2$). Such impurities in the metal oxide are desired to be not greater than 1% by weight, preferably not greater than 0.1% by weight.

The MgO carrier may be in a customarily employed form, such as powder, granules, spheres, cylinders, rods, rings or pellets. The MgO carrier having SA of 5 $m^2/g$ or less may be obtained by calcining a magnesium compound such as magnesium hydroxide, magnesium carbonate or basic magnesium carbonate at 1,000–1,500° C., preferably at 1,100–1,300° C. Generally commercially available magnesium oxide having SA of more than 5 $m^2/g$ may also be used as the magnesium compound. The calcination is generally carried out in air or in an inert atmosphere of for example nitrogen for at least 1 hour, preferably 3–72 hours.

The thus obtained MgO carrier having SA of 5 $m^2/g$ or less has a high degree of crystallinity and has stable surfaces having reduced strong acid sites. Namely, the MgO substrate has a Hammett acidity function (Ho) of 2 or more and has an amount of the acid sites of not greater than 0.03 mmol/g.

When SA of the MgO carrier is greater than 5 $m^2/g$, the degree of crystallinity becomes low and the amount of catalytic metal (Rh or Ru) supported thereon is unavoidably increased. Additionally, the acid strength is so increased that the resulting catalyst may cause undesirable reactions resulting in deposition of carbon on the catalyst. When SA of the MgO carrier is extremely low, the amount of the catalytic metal supported thereon is very small. At least 0.01 $m^2/g$ is desirable to obtain satisfactory catalytic activity. Preferably, SA of the MgO carrier is 0.05–3 $m^2/g$.

The catalytic metal may be supported on the MgO carrier by any known method. Equilibrium adsorption (disclosed in "Catalyst Preparation Chemistry" 1980, Kodansha Scientific, p. 49) is suitably adopted in which the carrier is immersed in an aqueous solution having a pH of 8 or more, preferably 8.5–13, and containing a water soluble catalytic metal such as halide, nitrate, sulfate, organic acid salt (e.g. acetate) or complex (chelate compound) of rhodium or ruthenium for at least 1 hour, preferably at least 3 hours. The immersion time is generally 48 hours or less. An alkali such as sodium hydroxide, potassium hydroxide, calcium hydroxide or magnesium hydroxide may be used for adjusting the pH of the solution.

The amount of the catalytic metal (Rh and/or Ru) supported on the MgO carrier is 10–5,000 ppm, preferably 10–4,000 ppm, more preferably 100–2,000 ppm, in terms of elemental metal, based on the weight of the carrier and is preferably controlled according to the specific surface area of the MgO carrier. An amount of the catalytic metal above 5,000 ppm is undesirable because the costs of the catalyst increase and because carbon deposition occurs. Too small an amount of the catalytic metal below 10 ppm fails to provide satisfactory catalytic activity. The amount of the catalytic metal may be controlled by control of the concentration of solution thereof in which the MgO carrier is immersed.

The MgO carrier to which the catalytic metal has been adsorbed is then separated from the solution and is dried at a temperature of preferably 35° C. or lower, more preferably 10–25° C., for at least 6 hours, preferably 12–72 hours. By gently drying the catalyst, abrupt evaporation of water from the MgO carrier may be avoided and aggregation of the catalytic metal may be avoided. As a consequence, the catalytic metal can be uniformly supported on the MgO carrier in a highly dispersed state.

The dried carrier is then calcined at a temperature of preferably at least 200° C., more preferably at least 500–1100° C. in air or in an atmosphere of inert gas for at least 2 hours, preferably 3–24 hours.

The above catalyst preparation method may be modified in various manners. For example, conventional impregnation, immersion, ion exchange may be adopted for supporting the catalytic metal on the carrier.

When MgO is used as a raw material for the MgO carrier having SA of 5 m²/g or less, it is preferred that the MgO raw material be molded using a binder into a desired form such as tablets, cylinders, hollow cylinders or rings. The binder, which is preferably powder, is selected from carbon, fatty acids having 12–22 carbon atoms, magnesium salts of fatty acids having 12–22 carbon atoms, carboxymethyl cellulose, a magnesium salt of carboxymethyl cellulose and polyvinyl alcohol. The carbon may be graphite, carbon black or activated carbon. Examples of the fatty acids include lauric acid, myristic acid, palmitic acid, stearic acid and behenic acid.

In the production of molded MgO carrier, MgO powder having an average particle diameter of 1–1,000 μm, preferably 10–100 μm, is mixed with a powder of the binder having an average particle diameter of 1–1,000 μm, preferably 10–100 μm to obtain a mixture. The binder is used in an amount of 0.1–5% by weight, preferably 0.5–3.0% by weight, based on the total weight of the binder and the MgO. The mixture is then molded, for example, by compression molding or by a tablet making method into a desired shape such as tablet, cylinder, ring, rod, etc. The molding is generally performed at room temperature and a pressure of 100–3,000 kg/cm²G, preferably 200–2,000 kg/cm²G. The size of the molded body may be suitably determined according to the kind of the catalyst bed adopted and is generally such that the major axis thereof has a length of 3–30 mm, preferably 5–25 mm. The molded carrier has good handling property and, when calcined, exhibits high mechanical strengths of, for example, a compression strength of 30–70 kg in the radial direction.

When MgO of the molded carrier has a low degree of crystallinity, the carrier is calcined at a temperature of 1,000° C. or higher to obtain a molded MgO carrier having SA of 5 m²/g or less and high mechanical strengths. During the course of the calcination, the binder contained in the molded carrier is decomposed and disappears. The resulting carrier is very suited as a carrier for use in the present invention.

The thus obtained synthesis gas having a molar ratio of hydrogen to carbon monoxide of 1.5–2.5 is then subjected to FT synthesis conditions, while the synthesis gas having a molar ratio of hydrogen to carbon monoxide of 0.5–1.5 is subjected to dimethyl ether synthesis conditions.

There are two types of FT synthesis catalysts. One of them is a relatively low CO shift reaction activity catalyst containing Co and/or Ru as a catalyst metal, the other being a relatively high CO shift reaction activity catalyst containing Fe as a catalyst.

With the former catalyst, the following reaction (5) occurs to yield hydrocarbons (represented by —CH₂—).

$$CO+2H_2 \rightarrow (-CH_2-)+H_2O \tag{5}$$

When the latter, iron catalyst is used, on the other hand, the following reaction (6) occurs in addition to the reaction (5):

$$CO+H_2O \rightarrow H_2+CO_2 \tag{6}$$

Thus, the overall reaction is as follows:

$$2CO+2H_2 \rightarrow (-CH_2-)+CO_2 \tag{7}$$

In the case of the iron catalyst, therefore, carbon conversion is 50% at maximum. Further, since an excess H₂ fed to the FT synthesis reactor accumulates therein, it is necessary to use a long residence time, which in turn requires a large volume reactor.

In contrast, the use of the low CO shift reaction activity catalyst can accomplish much higher carbon conversion and, therefore, is preferred for the purpose of the present invention. The preferred catalyst includes cobalt and/or ruthenium supported on a suitable carrier. One or more co-catalysts or promoters may also be contained in the catalyst. Illustrative of suitable co-catalysts are rhenium and noble metals such as platinum and palladium. Illustrative of suitable promoters are metals of Groups IA, IIA, IIIA, IIIB, IVA, IVB, VA and VIB of the Periodic Table, actinides and lanthanides. Above all, the use of oxides of Group IIA and IVB, such as titanium and zirconium, as a promoter is especially preferred for reasons of improved selectivity to higher molecular weight hydrocarbons. As the carrier, a refractory material and/or a silicate is preferably used. Particularly preferred is the use of silica, silica-alumina, alumina, synthetic zeolite and mixtures thereof. The amount of Co and/or Ru is 5–40 parts by weight per 100 parts by weight of the carrier.

The FT synthesis catalyst may be prepared by any conventionally employed method such as precipitation, fusion or impregnation. The FT synthesis catalysts may also be prepared by the methods disclosed in EP-A-0104672, EP-A-0110449, EP-A-0127220, EP-A-0167215, EP-A-0180269, EP-A-0221598, EP-A-0428223, JP-B-H05-34056, JP-A-H05-146679 and JP-A-H04-228428, the disclosure of which is hereby incorporated by reference herein. Characteristics of FT synthesis catalysts are described in "Fischer-Tropsch and Methanol Synthesis", R. A. Fiato et al, Topics in Catalysis, vol. 2, No. 1–4, 1995, Balzer Science Publishers, and "The Fischer-Tropsch Synthesis", R. B. Anderson, 1984, Academic Press, Inc., the disclosure of which is hereby incorporated by reference herein.

FT synthesis may be carried out by contacting a synthesis gas with the above FT synthesis catalyst at an elevated temperature, generally 125–350° C., preferably 175–300° C. and an elevated pressure, generally 5–100 atm, preferably 10–30 atm, using a reactor such as a fixed bed reactor, a fluidized bed reactor or a slurry phase reactor. FT synthesis reactors are disclosed in, for example, "Industrial Catalytic Reactions II", Shokubai Koza, vol. 9, p84–129, edited by Catalyst Academy, published by Kodansha Scientific, 1989;

and "Fischer-Tropsch Synthesis in Slurry Phase", M. D. Schlesinger et al, Engineering and Process Development, vol. 43, No. 6, 1951, p1474–1479, the disclosure of which is hereby incorporated by reference herein.

The reaction product obtained by FT synthesis is in the form of a high temperature gas of 125–350° C. containing hydrocarbons, unreacted $H_2$, CO and $H_2O$ and other gases such as $CO_2$ and $N_2$. The hydrocarbons may be separated by any suitable method. One suitable method includes introducing the reaction product into a high temperature and high pressure gas-liquid separator to separate the product into a gas phase containing $H_2$, CO, $CO_2$ and other gases and vapors of $H_2O$ and light hydrocarbons, and a liquid phase containing heavy hydrocarbons such as wax. The gas phase is then introduced into a low temperature and high pressure separator where it is separated into $H_2$, CO, $CO_2$ and other gases and a liquid phase containing $H_2O$ and light hydrocarbons.

The light hydrocarbon oil thus separated is composed of hydrocarbons having a wide range of molecular weights. It is known that the molecular weight distribution of hydrocarbons produced by FT synthesis accords with the Schulz-Flory distribution which is determined by chain growth probability α ("$C_1$ Chemistry", page 37–75, edited by Academy of Catalyst, Kodansha Scientific (1984)). The probability α varies between 0 and 1 according to the catalyst used and reaction conditions. Once α is determined, however, the carbon distribution is substantially unconditionally determined without depending upon conversion. As α increases, the molecular weight distribution shifts toward the longer chain side. In order to minimize light gas fractions having a small number of carbon atoms, therefore, α is desired to be as large as possible. In particular α is set at a value of 0.9 or more.

If desired, the hydrocarbons separated from the FT synthesis product may be subjected to catalytic hydrotreatment for the purpose of stabilizing olefins and oxygen-containing compounds contained therein by hydrogenation, isomerizing olefins to obtain an isoparaffin-rich product, and of hydrocracking heavy hydrocarbons to obtain a high quality middle fraction. The term "middle fraction" used herein is intended to refer to a mixed hydrocarbon oil corresponding to a kerosene and gas oil fraction obtained by topping of a petroleum crude. The middle fraction generally is a fraction of between about 100 and about 360° C. In the middle fraction, a fraction boiling between about 200 and 360° C. is generally called gas oil.

Thus, in one preferred embodiment according to the present invention, the hydrocarbon oil separated from the FT synthesis product is subjected to catalytic hydrotreatment at a high temperature and a high pressure to obtain high grade gasoline, kerosene and gas oil. In another preferred embodiment, heavy hydrocarbons separated from the hydrocarbon oil from the FT synthesis product are subjected to catalytic hydrocracking at a high temperature and a high pressure to obtain high grade gasoline, kerosene and gas oil.

As a raw material for the catalytic hydrotreatment is preferably a fraction obtained from the FT synthesis product and composed of hydrocarbons having at least 5 carbon atoms, preferably at least 9. The main reactions in the catalytic hydrotreatment include hydrogenation and hydroisomerization of light hydrocarbons and hydrocracking of heavy hydrocarbons.

Various known catalysts may be used for the catalytic hydrotreatment. Catalytic metals may be those of Groups VIB and VIII. Illustrative of suitable catalytic metals are Mo, W, Co, Ni, Ru, Ir, Os, Pt, Pd and a combination of two or more thereof. Above all, the use of Ni, Pt, Pd or a combination thereof is particularly preferred. The catalytic metal is generally supported by a refractory metal oxide or silicate. The carrier may be amorphous or crystalline. Examples of suitable carriers include silica, alumina, silica-alumina, zirconia, titania and a mixture thereof. One or more zeolite materials may be suitably used as a carrier by themselves or together with one or more of the above oxides. The amount of the catalytic metal varies with the kind thereof but is generally 0.05–80 parts by weight, preferably 1–70 parts by weight, in terms of elemental metal, per 100 parts by weight of the catalyst. It is preferred that the catalyst contain 0.05–2 parts by weight, more preferably 0.1–1 part by weight, of Pt.

The catalytic hydrotreatment may be carried out with a fluidized bed, a moving bed, a slurry bed or a fixed bed system, at a temperature of generally 175–400° C., preferably 250–375° C., and a hydrogen partial pressure of generally 10–250 atm, preferably 25–150 atm. When a fixed bed system is adopted, the raw material feed is preferably treated at a weight space hourly velocity of 0.1–5 kg/hour, more preferably 0.25–2 kg/hour. Hydrogen is generally fed at a gas space hourly velocity of 100–10,000 Nl/hour, preferably 500–5,000 Nl/hour. The ratio of hydrogen and the raw material feed is in the range of 100–5,000 Nl/kg.

The hydrocarbons obtained by the catalytic hydrotreatment are generally separated by distillation into light fraction, middle fraction and heavy residues. At least a part of the heavy residues may be recycled to the hydrotreatment for the conversion into a middle fraction.

In one preferred embodiment according to the present invention, at least part of the light hydrocarbon fraction containing olefins, alcohols and aldehydes may be recycled to the FT synthesis reactor to shift the selectivity of the FT synthesis toward higher molecular weight compounds and to improve yield of a middle fraction. The olefines, alcohols and aldehydes thus recycled to the FT synthesis reactor are adsorbed on the catalyst and subjected to further chain growing reactions.

In another preferred embodiment, at least a part of a gas product obtained by removing hydrocarbons from the FT synthesis product and containing $CH_4$, $CO_2$ and $H_2$ is recycled to the previously described distillation tower operated for controlling the $CO_2$ content in the raw material HC. Alternatively, such a gas product may be used as a fuel for the reformer for the production of the synthesis gas or as a fuel for producing high temperature gas for use in a generator gas turbine.

In another aspect of the present invention, the synthesis gas having a molar ratio of hydrogen to carbon monoxide of 0.5–1.5 is subjected to dimethyl ether synthesis using one or more catalysts which, either alone or in combination, exhibit activities of methanol synthesis, methanol dehydration or CO shift reaction. The reactions of the synthesis gas resulting in the formation of dimethyl ether are as follows:

$$2H_2 + CO \rightarrow CH_3OH \tag{8}$$

$$2CH_3OH \rightarrow CH_3OCH_3 + H_2O \tag{9}$$

$$CO + H_2O \rightarrow CO_2 + H_2 \tag{10}$$

Overall reaction is thus:

$$3CO + 3H_2 \rightarrow CH_3OCH_3 + CO_2 \tag{11}$$

The catalyst used for the production of dimethyl ether from the synthesis gas may be a single catalyst effective for the reactions (8)–(10) or a combination of a first catalyst effective for one or two of the reactions (8)–(10) and a second catalyst effective for the other reaction or reactions (8)–(10). Three kinds of catalysts effective for respective reactions (8)–(10) may be also used. Examples of catalysts effective for the methanol synthesis (8) include CuO—ZnO supported on a chromium oxide or alumina carrier. Methanol synthesis catalysts generally have also an activity for catalyzing the CO shift reaction (10). Examples of catalysts effective for the methanol dehydration (9) include metal oxide catalysts, such as $Al_2O_3$, $SiO_2.Al_2O_3$, $ThO_2$, $TiO_3$, $ZrO_3$, zeolite, layered silicate and ion exchange resins. Examples of catalysts effective for CO shift reactions (10) include Fe.Cr catalysts, Cu.Zn catalysts and Cu.Cr.Zn catalysts.

The dimethyl ether synthesis is generally performed at a temperature of 150–400° C. and a pressure of 20–100 kg/cm²G using a fixed bed, fluidized bed, suspension bed or moving bed.

The following examples will further illustrate the present invention. Parts are by weight.

EXAMPLE 1

Catalyst Preparation

97 Parts of commercially available MgO powder (purity: 98.1% or more) were mixed with 3 parts of carbon powder (binder) and the mixture was subjected to tablet making to obtain pellets having ⅛ inch size. The pellets were calcined at 1,100° C. for 3 hours in air to obtain a MgO carrier I. MgO carrier I was then immersed in an aqueous solution of rhodium acetate for about 12 hours so that Rh was adsorbed on the carrier to obtain Rh-loaded MgO carrier I. The amount of Rh supported on the MgO carrier I was 0.075%, in terms of elemental Rh, based on the weight of the MgO carrier I. The Rh-loaded MgO carrier I was then dried in air at room temperature for about 24 hours and calcined at 900° C. for 3 hours in air, thereby obtaining Catalyst I having a specific surface area of 0.6 m²/g.

EXAMPLE 2

Catalyst Preparation

98 Parts of commercially available MgO powder (purity: 98.1% or more) were mixed with 2 parts of carbon powder and the mixture was subjected to tablet making to obtain pellets having ⅛ inch size. The pellets were calcined at 1,050° C. for 3 hours in air to obtain a MgO carrier II. MgO carrier II was then immersed in a methanol solution of ruthenium acetonate for about 12 hours so that Ru was adsorbed on the carrier to obtain Ru-loaded MgO carrier II. The amount of Ru supported on the MgO carrier II was 0.1%, in terms of elemental Ru, based on the weight of the MgO carrier II. The Ru-loaded MgO carrier II was then dried in air at room temperature for about 24 hours and calcined at 800° C. for 3 hours in air, thereby obtaining Catalyst II having a specific surface area of 1.1 m²/g.

EXAMPLE 3

Catalyst Preparation Example

97 Parts of commercially available MgO powder (purity: 98.7% or more) were mixed with 3 parts of carbon powder and the mixture was subjected to tablet making to obtain pellets having ⅛ inch size. The pellets were calcined at 1,060° C. for 3 hours in air to obtain a MgO carrier III. MgO carrier III was then immersed in an aqueous solution containing 3.9% by weight, in terms of Rh metal, of rhodium acetate and having a pH of 9.7 for 26 hours so that Rh was adsorbed on the carrier by equilibrium adsorption to obtain Rh-loaded MgO carrier III. The amount of Rh supported on the MgO carrier III was 3,750 ppm, in terms of elemental Rh, based on the weight of the MgO carrier III. The Rh-loaded MgO carrier III was then dried in air at 35° C. for 52 hours and calcined at 850° C. for 3 hours in air, thereby obtaining Catalyst III having a Rh content of 3,750 ppm, in terms of elemental Rh, a specific surface area of 1.2 m²/g. Acid sites of catalyst III had an acid strength (Ho) of 3.3 or more and were present in an amount of 0.01 mmol/g.

EXAMPLE 4

Catalyst Preparation

Commercially available MgO powder (purity: more than 99.9%) was formed into pellets having ⅛ inch size and calcined at 1,000° C. for 2 hours in air to obtain a MgO carrier IV. MgO carrier IV was then immersed in an aqueous solution containing 0.1% by weight, in terms of Ru metal, of ruthenium (III) chloride and having a pH of 9.7 for 19 hours so that Ru was adsorbed on the carrier by equilibrium adsorption to obtain Ru-loaded MgO carrier IV. The amount of Ru supported on the MgO carrier IV was 125 ppm, in terms of elemental Ru, based on the weight of the MgO carrier IV. The Rh-loaded MgO carrier IV was then dried in air at 30° C. for 72 hours and calcined at 860° C. for 2.5 hours in air, thereby obtaining Catalyst IV having a Ru content of 125 ppm by weight, in terms of elemental Ru, a specific surface area of 4.8 m²/g. Acid sites of catalyst IV had an acid strength (Ho) of 3.3 or more and were present in an amount of 0.03 mmol/g.

EXAMPLE 5

Catalyst Preparation

Commercially available MgO powder (purity: 98.0%) was molded to obtain pellets having ⅛ inch size. The pellets were calcined at 1,200° C. for 2.5 hours in air to obtain a MgO carrier V. MgO carrier V was then immersed in an aqueous solution containing 2.6% by weight, in terms of Rh metal, of rhodium acetate and having a pH of 9.7 for 26 hours so that Rh was adsorbed on the carrier by equilibrium adsorption. This was filtered to obtain Rh-loaded MgO carrier V. The amount of Rh supported on the MgO carrier V was 1,750 ppm, in terms of elemental Rh, based on the weight of the MgO carrier V. The Rh-loaded MgO carrier V was then dried in air at 20° C. for 34 hours and calcined at 950° C. for 3.5 hours in air, thereby obtaining Catalyst V having a Rh content of 1,750 ppm, in terms of elemental Rh, a specific surface area of 0.2 m²/g. Acid sites of catalyst V had an acid strength (Ho) of 3.3 or more and were present in an amount of 0.002 mmol/g.

EXAMPLE 1

Comparative Catalyst Preparation

The particle size of magnesium oxide calcined at 370° C. for 3 h in air was adjusted to 0.27–0.75 mm. Thereafter, Rh was supported on the magnesium oxide by an impregnation method. This was further calcined at 370° C. in air to obtain a Rh-supporting MgO catalyst (Rh content was 0.10 mol % based on MgO). The above impregnated material was obtained by adding dropwise an aqueous solution of rhodium(III) acetate extremely little by little to the calcined MgO, with mixing by shaking after each dropwise addition. The rhodium(III) acetate aqueous solution had a Rh concentration of 1.7% by weight. The Rh-impregnated material was dried at 120° C. for 2.5 hours in air and calcined at 370° C. for 3 hours in the same atmosphere to obtain the Rh-supporting MgO catalyst (Comparative Catalyst) having a surface area of 98 m²/g.

$CO_2$ Distillation Example

A natural gas containing 50.2 mol % of $CO_2$, 44.7 mol % of methane, 4.5 mol % of ethane and 0.6 mol % of propane was distilled in a distillation tower having a theoretical plate number of 10 at a pressure of 30 kg/cm²G, a tower top temperature of −45.4° C. and a power bottom pressure of −5.0° C. with a reflux ratio of 1.0, thereby obtaining a topped fraction containing 30.0 mol % of $CO_2$, 63.8 mol % of methane, 6.1 mol % of ethane and 0.1 mol % of propane.

EXAMPLE 1

Preparation of Synthesis Gas

The topped fraction obtained in $CO_2$ Distillation Example was used as a raw material feed and contacted with a fixed bed of Catalyst I to produce a synthesis gas. The catalyst I was previously subjected to a reduction treatment at 900° C. for 1.5 hours in a $H_2$ stream. The raw material feed was mixed with $H_2O$ to provide a molar ratio of the $H_2O$ to the total moles of the lower hydrocarbons contained in the raw material feed of 1:0.99 (($[CO_2]+[H_2O])/[C]=1.38$). The reaction was performed at a temperature (temperature at an exit of the catalyst bed) of 900° C. and a pressure of 20 kg/cm²G and with GHSV (based on a total amount of the gas at an inlet) of 4,500 hr⁻¹. The $CH_4$ conversion was 67%. The synthesis gas thus obtained had a $H_2$ content of 50.0 mol %, a CO content of 24.9 mol % ($H_2/CO=2.0$), a $CH_4$ content of 7.5 mol %, a $CO_2$ content of 4.8 mol % and a $H_2O$ content of 12.8 mol %.

FT Synthesis

The thus obtained synthesis gas was cooled to remove $H_2O$ and subjected to FT synthesis. A catalyst having, supported on $SiO_2$, 15% by weight of Co as a catalytic metal and 1.2% by weight of Zr as a promoter was packed in a reactor. The synthesis gas feed was reacted in the reactor at a temperature of 220° C., a pressure of 20 kg/cm²G and a GHSV (synthesis gas feed basis) of 1500 hr⁻¹. The CO conversion was 75%. The product of FT synthesis had the composition shown in Table 1 below.

TABLE 1

| Hydrocarbon | Content (% by weight) |
|---|---|
| Light HC gas (C4 or lower) | 2.5 |
| Naphtha (C5 to C11) | 48.8 |
| Kerosene and gas oil (C12–C22) | 21.1 |
| Wax (C23 or higher) | 27.6 |

Hydrocracking of Product of FT Synthesis

The above product of FT synthesis was separated into a light fraction of C22 or lower and a heavy fraction of C23 or higher. The heavy fraction was subjected to hydrocracking using a catalyst containing 5.1% by weight of Mo and 2.8% by weight of W supported on $SiO_2/Al_2O_3$ carrier at a temperature of 320° C., a pressure of 45 kg/cm²G and a LHSV of 0.5 hr⁻¹ with a hydrogen to oil ratio ($H_2$ N liter/Oil liter) of 2000. The compositions of the heavy fraction and the hydrocracked product are shown in Table 2.

TABLE 2

| | Content (% by weight) | |
|---|---|---|
| Hydrocarbon | Heavy Fraction | Product |
| Light HC gas (C4 or lower) | — | 2.3 |
| Naphtha (C5 to C11) | — | 22.5 |
| Kerosene and gas oil (C12–C22) | 4.2 | 43.3 |
| Wax (C23 or higher) | 95.8 | 31.9 |

EXAMPLE 2

Preparation of Synthesis Gas

The catalyst I (30 cc) obtained in Catalyst Preparation Example 1 was packed in a reactor to perform a test of reforming methane with $CO_2$.

The catalyst was previously subjected to a reduction treatment at 900° C. for 1 hour in a $H_2$ stream. A mixed gas having ($[CO_2]+[H_2O])/[C]$ ratio of 1.02 was then treated at a temperature of 850° C. (temperature at the exit of the catalyst layer) and a pressure of 20 kg/cm²G and with GHSV (gas feed basis) of 5,000 hr⁻¹. The product gas had $H_2/CO$ molar ratio of 2.0. The synthesis gas production efficiency Yf and the carbon conversion efficiency Cf at 5 hours after the commencement of the reaction were 102% and 52%, respectively. The synthesis gas production efficiency Yf and the carbon conversion efficiency Cf at 3000 hours after the commencement of the reaction were 101% and 52%, respectively.

EXAMPLE 3

Preparation of Synthesis Gas

The catalyst II (30 cc) obtained in Catalyst Preparation Example 2 was packed in a reactor to perform a synthesis gas production test in the same manner as that described in Example 1. The product gas had $H_2/CO$ molar ratio of 2.0. The synthesis gas production efficiency Yf and the carbon conversion efficiency Cf at 5 hours after the commencement of the reaction were 103% and 53%, respectively. The synthesis gas production efficiency Yf and the carbon conversion efficiency Cf at 4,000 hours after the commencement of the reaction were 103% and 53%, respectively.

EXAMPLE 4

Preparation of Synthesis Gas

The catalyst II (30 cc) obtained in Catalyst Preparation Example 2 was packed in a reactor to perform synthesis gas production tests using, as raw material feed, methane containing various amounts of $CO_2$ as shown in Table 3-1. An amount of $H_2O$ was added to each raw material feed so that the synthesis gas produced had a $H_2/CO$ molar ratio of 2.0. The ($[CO_2]+H_2O])/[CH_4]$ ratios of the mixed gases were as shown in Table 3-1. Mixed gases shown in Table 3-1 were each treated at a temperature of 850° C. (temperature at the exit of the catalyst layer) and a pressure of 20 kg/cm²G and with GHSV (gas feed basis) of 4,000 hr⁻¹. The catalyst was previously subjected to a reduction treatment at 900° C. for 2 h in a $H_2$ stream. The synthesis gas production efficiency Yf and the carbon conversion efficiency Cf at 500 hours after the commencement of the reaction in each test were as summarized in Table 3-2. From the results shown in Table 3-1 and 3-2, it is evident that satisfactory synthesis gas production efficiency Yf and carbon conversion efficiency Cf are obtained when the raw material feed satisfies the condition:

$$0.5 \leq ([CO_2]+[H_2O])/[C] \leq 2.5.$$

TABLE 3-1

| $CO_2$ Concentration in Raw Material Feed (mol %) | Flow Rate of Components of Mixed Gas (mol/hr) | | | | $\frac{CO_2 + H_2O}{CH_4}$ |
|---|---|---|---|---|---|
| | $CH_4$ | $H_2O$ | $CO_2$ | Total | |
| 8.91 | 5.16 | 1.03 | 0.50 | 6.70 | 0.30 |
| 19.2 | 3.86 | 1.93 | 0.91 | 6.70 | 0.74 |
| 27.2 | 3.08 | 2.47 | 1.15 | 6.70 | 1.17 |
| 33.7 | 2.57 | 2.82 | 1.30 | 6.70 | 1.61 |
| 39.1 | 2.20 | 3.08 | 1.41 | 6.70 | 2.04 |
| 43.7 | 1.93 | 3.28 | 1.49 | 6.70 | 2.48 |
| 47.6 | 1.71 | 3.43 | 1.56 | 6.70 | 2.91 |
| 57.4 | 1.25 | 3.75 | 1.69 | 6.70 | 4.35 |

TABLE 3-2

| Flow Rate of Products (mol/hr) | | | | | | Yf *1 | Cf *2 |
|---|---|---|---|---|---|---|---|
| $CH_4$ | $H_2O$ | $CO_2$ | $H_2$ | CO | Total | (%) | (%) |
| 3.88 | 0.18 | 0.08 | 3.42 | 1.71 | 9.26 | 76.6 | 30.2 |
| 2.17 | 0.80 | 0.35 | 4.50 | 2.25 | 10.07 | 100.7 | 47.1 |
| 1.37 | 1.33 | 0.58 | 4.55 | 2.28 | 10.11 | 102.0 | 53.8 |
| 0.92 | 1.73 | 0.76 | 4.38 | 2.19 | 9.98 | 98.1 | 56.6 |
| 0.65 | 2.05 | 0.90 | 4.14 | 2.07 | 9.80 | 92.8 | 57.3 |
| 0.47 | 2.30 | 1.01 | 3.89 | 1.95 | 9.62 | 87.2 | 56.9 |
| 0.34 | 2.51 | 1.10 | 3.52 | 1.78 | 9.26 | 79.1 | 54.3 |
| 0.14 | 3.01 | 1.32 | 2.99 | 1.46 | 8.92 | 66.4 | 49.7 |

*1: Synthesis gas production efficiency
Yf = {[CO] + [H$_2$])/([CH$_4$] + [CO$_2$] + [H$_2$O])} × 100% wherein [CO] + [H$_2$] is a total flow rate of CO and H$_2$ in the product stream and [CH$_4$] + [CO$_2$] + [H$_2$O] is a total flow rate of CH$_4$, CO$_2$ and H$_2$O in the mixed gas
*2: Carbon conversion efficiency
Cf = {[CO]/([CH$_4$] + [CO$_2$])} × 100% wherein [CO] is a flow rate of CO in the product stream and [CH$_4$] + [CO$_2$] is a total flow rate of CH$_4$ and CO$_2$ in the mixed gas

COMPARATIVE EXAMPLE 1

Preparation of Synthesis Gas in Example 1 was repeated in the same manner as described except that Comparative Catalyst obtained in Comparative Catalyst Preparation Example 1 was substituted for Catalyst I. The $CH_4$ conversion efficiencies at 5 and 500 hours after the commencement of the reaction were 53% and 40.0%, respectively. The catalytic activity was rapidly lost.

EXAMPLE 5

Preparation of Synthesis Gas

The topped fraction obtained in $CO_2$ Distillation Example was used as a raw material feed and contacted with a fixed bed of Catalyst I to produce a synthesis gas. The catalyst I was previously subjected to a reduction treatment at 900° C. for 1.5 hours in a $H_2$ stream. The raw material feed was mixed with $H_2O$ to provide a molar ratio of the $H_2O$ to the total moles of the lower hydrocarbons contained in the raw material feed of 1:0.36 (($[CO_2]+[H_2O])/[C]=1.28$). The reaction was performed at a temperature (temperature at an exit of the catalyst bed) of 900° C. and a pressure of 20 kg/cm$^2$G and with GHSV (based on a total amount of the gas at an inlet) of 4,500 hr$^{-1}$. The $CH_4$ conversion was 67%. The synthesis gas thus obtained had a $H_2$ content of 38.5 mol %, a CO content of 38.5 mol % ($H_2$/CO=1.0), a $CH_4$ content of 7.7 mol %, a $CO_2$ content of 6.5 mol % and a $H_2O$ content of 8.8 mol %.

Dimethyl Ether Synthesis

The thus obtained synthesis gas was cooled to remove $H_2O$ and subjected to dimethyl ether synthesis. A methanol synthesis catalyst (15 cc) of a Cu—Zn—Al system (CuO: 42% by weight, ZnO: 47% by weight and Al$_2$O$_3$: 11% by weight) and a methanol dehydration catalyst (15 cc) having CuO supported on γ-Al$_2$O$_3$ were physically mixed and packed in a reactor. The synthesis gas feed was reacted in the reactor at a temperature of 250° C., a pressure of 50 kg/cm$^2$G and a GHSV of 4,000 hr$^{-1}$. The CO conversion was 84.7%. The yield of dimethyl ether from the synthesis gas was 42.9%.

EXAMPLE 6

Preparation of Synthesis Gas

The catalyst I (30 cc) obtained in Catalyst Preparation Example 1 was packed in a reactor to perform a synthesis gas production. The catalyst I was previously subjected to a reduction treatment at 900° C. for 1 hour in a $H_2$ stream. The raw material feed was mixed with $H_2O$ to provide ($[CO_2]+[H_2O])/[C]$ ratio of 1.82. The reaction was performed at a temperature (temperature at an exit of the catalyst bed) of 850° C. and a pressure of 20 kg/cm$^2$G and with GHSV (raw material feed basis) of 5,000 hr$^{-1}$. The product gas had a $H_2$/CO molar ratio of 1.0. The synthesis gas production efficiency Yf and the carbon conversion efficiency Cf at 5 hours after the commencement of the reaction were 98% and 62%, respectively. The synthesis gas production efficiency Yf and the carbon conversion efficiency Cf at 2,000 h after the commencement of the reaction were 98% and 62%, respectively.

EXAMPLE 7

Preparation of Synthesis Gas

The catalyst II (30 cc) obtained in Catalyst Preparation Example 2 was packed in a reactor to perform a synthesis gas production test in the same manner as that described in Example 6. The product gas had $H_2$/CO molar ratio of 1.0. The synthesis gas production efficiency Yf and the carbon conversion efficiency Cf at 5 hours after the commencement of the reaction were 97% and 61%, respectively. The synthesis gas production efficiency Yf and the carbon conversion efficiency Cf at 1,500 hours after the commencement of the reaction were 96% and 60%, respectively.

EXAMPLE 8

Preparation of Synthesis Gas

The catalyst I (30 cc) obtained in Catalyst Preparation Example 1 was packed in a reactor to perform synthesis gas production tests using, as raw material feed, methane containing various amounts of $CO_2$ as shown in Table 4-1. An amount of $H_2O$ was added to each raw material feed so that the synthesis gas obtained had a $H_2$/CO molar ratio of 1.0. The ($[CO_2]+[H_2O])/[CH_4]$ ratios of the mixed gas were as shown in Table 4-1. Mixed gases shown in Table 4-1 were each treated at a temperature of 850° C. (temperature at the exit of the catalyst layer) and a pressure of 20 kg/cm²G and with GHSV (gas feed basis) of 4,000 hr⁻¹. The catalyst was previously subjected to a reduction treatment at 900° C. for 2 h in a $H_2$ stream. The synthesis gas production efficiency Yf and the carbon conversion efficiency Cf at 500 hours after the commencement of the reaction in each test were as summarized in Table 4-2. From the results shown in Tables 4-1 and 4-2, it is evident that satisfactory synthesis gas production efficiency Yf and carbon conversion efficiency Cf are obtained when the raw material feed satisfies the condition:

$$0.5 \leq ([CO_2]+[H_2O])/[C] \leq 2.5.$$

TABLE 4-1

| $CO_2$ Concentration in Raw Material Feed (mol %) | Flow Rate of Components of Mixed Gas (mol/hr) | | | | $\frac{CO_2 + H_2O}{CH_4}$ |
|---|---|---|---|---|---|
| | $CH_4$ | $H_2O$ | $CO_2$ | Total | |
| 20.6 | 4.19 | 0.08 | 1.08 | 5.36 | 0.28 |
| 32.6 | 3.38 | 0.34 | 1.64 | 5.36 | 0.58 |
| 45.2 | 2.52 | 0.76 | 2.08 | 5.36 | 1.13 |
| 57.2 | 1.76 | 1.23 | 2.36 | 5.36 | 2.04 |
| 61.0 | 1.55 | 1.39 | 2.42 | 5.36 | 2.46 |
| 66.5 | 1.25 | 1.63 | 2.48 | 5.36 | 3.28 |
| 72.0 | 0.98 | 1.86 | 2.51 | 5.36 | 4.47 |

TABLE 4-2

| Flow Rate of Products (mol/hr) | | | | | | Yf *1 | Cf *2 |
|---|---|---|---|---|---|---|---|
| $CH_4$ | $H_2O$ | $CO_2$ | $H_2$ | CO | Total | (%) | (%) |
| 3.18 | 0.08 | 0.07 | 2.02 | 2.02 | 7.38 | 75.5 | 38.4 |
| 2.04 | 0.34 | 0.30 | 2.68 | 2.68 | 8.04 | 100.0 | 53.4 |
| 1.10 | 0.76 | 0.66 | 2.84 | 2.84 | 8.19 | 105.9 | 61.6 |
| 0.48 | 1.23 | 1.08 | 2.56 | 2.56 | 7.92 | 95.6 | 62.1 |
| 0.34 | 1.39 | 1.22 | 2.40 | 2.40 | 7.76 | 89.7 | 60.6 |
| 0.19 | 1.63 | 1.42 | 2.12 | 2.12 | 7.47 | 79.1 | 56.7 |
| 0.09 | 1.86 | 1.63 | 1.82 | 1.72 | 7.12 | 66.0 | 49.1 |

Yf and Cf are as defined in Table 3-2.

COMPARATIVE EXAMPLE 2

Preparation of Synthesis Gas in Example 5 was repeated in the same manner as described except that Comparative Catalyst obtained in Comparative Catalyst Preparation Example 1 was substituted for Catalyst I. The $CH_4$ conversion efficiencies at 5 and 200 hours after the commencement of the reaction were 65% and 37%, respectively. The catalytic activity was rapidly lost.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all the changes which come within the meaning and range of equivalency of the claims are therefore intended to be embraced therein.

The teachings of Japanese Patent Applications No. H10-292930 and No. H10-292931, both filed Sep. 30, 1998, inclusive of the specification and claims, are hereby incorporated by reference herein.

What is claimed is:

1. A process for the production of a liquid hydrocarbon oil, comprising the steps of:
   (a) mixing a gas feed, containing a lower hydrocarbon having 1–4 carbon atoms and 10–50 mole % of $CO_2$ based on a total mole of the $CO_2$ and the lower hydrocarbon, with $H_2O$ to obtain a mixed gas having contents of the $CO_2$, $H_2O$ and lower hydrocarbon satisfying the following condition:

$$0.5 \leq ([CO_2]+[H_2O])/[C] \leq 2.5$$

wherein $[CO_2]$ represents the moles of the $CO_2$, $[H_2O]$ represents the moles of the $H_2O$ and $[C]$ represents the moles of carbon of the lower hydrocarbon;
   (b) contacting said mixed gas with a catalyst at a temperature of 600–1,000° C. and a pressure of 10–75 atm to produce a synthesis gas with a carbon conversion efficiency Cf of at least 50% and a synthesis gas production efficiency Yf of at least 80%,
   said synthesis gas production efficiency Yf being represented by the following formula:

$$Yf = \{[CO]+[H_2])/([C]+[CO_2]+[H_2O])\} \times 100\%$$

wherein [CO] represents the moles of CO in said synthesis gas, $[H_2]$ represents the moles of $H_2$ in said synthesis gas, and $[CO_2]$, $[H_2O]$ and $[C]$ are as defined previously,
   said carbon conversion efficiency Cf being represented by the following formula:

$$Cf = \{[CO]/([C]+[CO_2])\} \times 100\%$$

wherein [CO], $[CO_2]$ and [C] are as defined previously,
   said synthesis gas having a molar ratio of hydrogen to carbon monoxide of 1.5–2.5,
   said catalyst having a specific surface area of 5 m²/g or less and comprising a magnesium oxide-containing carrier and at least one catalytic metal selected from the group consisting of rhodium and ruthenium and supported on said carrier in an amount of 10–5,000 ppm, in terms of elemental metal, based on the weight of said carrier;
   (c) reacting said synthesis gas in the presence of a Fischer-Tropsch catalyst having a low CO shift reaction activity to obtain a product containing a liquid hydrocarbon oil; and
   (d) separating said liquid hydrocarbon oil from said product.

2. A process as claimed in claim 1, wherein said gas feed contains 20–40 mole % of $CO_2$ and wherein said mixed gas satisfies the following condition:

$$1 \leq ([CO_2]+[H_2O])/[C] \leq 2$$

wherein $[CO_2]$, $[H_2O]$ and [C] are as defined in claim 1.

3. A process as claimed in claim 1, wherein said gas feed is discharged overhead from a distillation tower where a raw material feed containing $CO_2$ and a lower hydrocarbon is distilled at a pressure of 10–80 atm while removing $CO_2$ from a bottom thereof.

4. A process as claimed in claim 3, wherein said distillation tower is operated at a pressure of 20–50 atm and a tower top temperature of −60° C.

5. A process as claimed in claim 1, wherein said Fischer-Tropsch catalyst comprises Co and/or Ru as catalytic metal thereof.

6. A process as claimed in claim 1, further comprising subjecting said liquid hydrocarbon oil separated in step (d) to catalytic hydrogenation and/or catalytic hydrocracking to obtain gasoline, kerosene and gas oil.

7. A process as claimed in claim 1, further comprising separating a gas product containing methane, hydrogen and carbon dioxide from said product in step (d), and using at least part of said gas product as a heat energy source in step (b).

8. A process as claimed in claim 1, further comprising separating a light hydrocarbon fraction containing olefins from said product in step (d), and recycling at least part of said light hydrocarbon fraction to step (c).

* * * * *